(12) United States Patent
Beruda et al.

(10) Patent No.: US 8,735,646 B2
(45) Date of Patent: May 27, 2014

(54) DIAPER WITH IMPROVED BODY FIT

(75) Inventors: Holger Beruda, Schwalbach (DE); Yasue Nakagawa, Bad Soden (DE); Mattias Schmidt, Idstein (DE); Hiroyuki Ikeuchi, Himeji (JP); Kazushi Torii, Himeji (JP); Shigeru Sakamoto, Himeji (JP); Taku Iwamura, Himeji (JP); Sayaka Machida, Himeji (JP)

(73) Assignee: The Procter & Gamble Company, Cincinnati, OH (US)

( * ) Notice: Subject to any disclaimer, the term of this patent is extended or adjusted under 35 U.S.C. 154(b) by 1325 days.

(21) Appl. No.: 11/091,255

(22) Filed: Mar. 28, 2005

(65) Prior Publication Data

US 2005/0222547 A1  Oct. 6, 2005

Related U.S. Application Data

(60) Provisional application No. 60/612,926, filed on Sep. 24, 2004.

(51) Int. Cl.
*A61F 13/15* (2006.01)
*A61F 13/20* (2006.01)

(52) U.S. Cl.
USPC ............ 604/378; 604/367; 604/368; 604/381

(58) Field of Classification Search
USPC .................................. 604/378, 367, 368, 381
See application file for complete search history.

(56) References Cited

U.S. PATENT DOCUMENTS

| | | | |
|---|---|---|---|
| 4,610,678 A | | 9/1986 | Weisman et al. |
| 4,673,402 A | | 6/1987 | Weisman et al. |
| 4,699,620 A | * | 10/1987 | Bernardin ................ 604/385.25 |
| 4,834,735 A | * | 5/1989 | Alemany et al. .............. 604/368 |
| 4,935,022 A | * | 6/1990 | Lash et al. .................... 604/368 |
| 4,978,603 A | * | 12/1990 | Inoue et al. ................... 430/265 |
| 5,102,597 A | | 4/1992 | Roe et al. |
| 5,217,445 A | * | 6/1993 | Young et al. .................. 604/381 |
| 5,260,345 A | | 11/1993 | DesMarais et al. |
| 5,387,207 A | | 2/1995 | Dyer et al. |

(Continued)

FOREIGN PATENT DOCUMENTS

| | | |
|---|---|---|
| EP | 0 401 189 B2 | 12/1990 |
| JP | 2004-105118 | 4/2004 |

(Continued)

OTHER PUBLICATIONS

PCT International Search Report mailed Nov. 8, 2005 (17 pages).

*Primary Examiner* — Tatyana Zalukaeva
*Assistant Examiner* — Ginger T Chapman
(74) *Attorney, Agent, or Firm* — Andrew J. Mueller; Laura L. Whitmer; Eric T. Addington

(57) ABSTRACT

An absorbent article that has a thin, conformable absorbent core where the core has at least two layers, both of which are substantially free of cellulosic fibers is described. The first layer is intended to provide storage for the majority of acquired fluids and has an AAP of at least about 20 g/g and the second layer, which provides temporary capacity for the bulk of the acquired fluid and permanent storage for at least a portion thereof, comprises a second absorbent polymer material which has a Wet Permeability of at least about $400 \times 10^{-7}$ ($cm^3$ seconds)/g a ratio of Wet Permeability to SFC of at least about 1.5:1 with respect to the first absorbent polymer material.

14 Claims, 5 Drawing Sheets

(56) References Cited

U.S. PATENT DOCUMENTS

| | | | |
|---|---|---|---|
| 5,397,316 A | 3/1995 | LaVon et al. | |
| 5,411,497 A | 5/1995 | Tanzer et al. | |
| 5,439,458 A * | 8/1995 | Noel et al. | 604/378 |
| 5,569,234 A | 10/1996 | Buell et al. | |
| 5,599,335 A | 2/1997 | Goldman et al. | |
| 5,728,082 A | 3/1998 | Gustafsson et al. | |
| 5,836,929 A | 11/1998 | Bewick-Sonntag et al. | |
| 5,843,063 A * | 12/1998 | Anderson et al. | 604/378 |
| 5,868,724 A | 2/1999 | Dierckes, Jr. et al. | |
| 6,011,996 A | 1/2000 | Wang et al. | |
| 6,037,518 A * | 3/2000 | Guidotti et al. | 604/378 |
| 6,068,620 A * | 5/2000 | Chmielewski | 604/378 |
| 6,083,210 A * | 7/2000 | Young et al. | 604/367 |
| 6,232,520 B1 | 5/2001 | Hird et al. | |
| 6,479,415 B1 * | 11/2002 | Erspamer et al. | 442/381 |
| 6,710,225 B1 | 3/2004 | Everett et al. | |
| 7,837,662 B2 * | 11/2010 | Nakagawa et al. | 604/385.101 |
| 2002/0169430 A1 * | 11/2002 | Kirk et al. | 604/378 |
| 2003/0233082 A1 | 12/2003 | Kline et al. | |
| 2004/0162536 A1 | 8/2004 | Becker et al. | |
| 2004/0167486 A1 | 8/2004 | Busam et al. | |
| 2005/0013992 A1 | 1/2005 | Azad et al. | |
| 2005/0030280 A1 | 2/2005 | Gehlot et al. | |
| 2005/0101928 A1 | 5/2005 | Beruda et al. | |

FOREIGN PATENT DOCUMENTS

| | | |
|---|---|---|
| WO | WO 95/26209 A1 | 10/1995 |
| WO | WO 99/55263 A1 | 11/1999 |
| WO | WO 03/043670 A | 5/2003 |
| WO | WO 2004/018005 A1 | 3/2004 |
| WO | WO 2004/018006 A1 | 3/2004 |
| WO | WO 2004/069915 A2 | 8/2004 |
| WO | WO 2005/030278 A1 | 4/2005 |

* cited by examiner

DIAPER WITH IMPROVED BODY FIT

CROSS REFERENCE TO RELATED APPLICATION

This application claims the benefit of U.S. Provisional Application No. 60/612,926 filed Sep. 24, 2004.

FIELD OF THE INVENTION

The present invention concerns an absorbent article, preferably a disposable absorbent article, such as a diaper. The present invention specifically relates to an absorbent core for such an absorbent article that provides the article with improved softness and conformity to a wearer's body. This absorbent core is also useful for providing an absorbent article of increased wearing comfort.

BACKGROUND

Absorbent articles, such as diapers and adult incontinence products, are well known articles of commerce. Multiple attempts have been made to provide them with an overall good fit and with a high absorbent capacity. Modern diapers make use of absorbent polymer materials also known as superabsorbent polymers, which allow for storage of significant amounts of aqueous liquids (e.g., on the order 300 ml for a typical baby diaper).

While such an absorbent article is generally a disposable product, it is frequently worn over many hours and worn in a dry state as well as in a urine loaded state. As a result, providing good wearing comfort is very important both when the article is dry and when the article is fully or partially loaded with urine (or other bodily liquids).

One way the art has approached wearing comfort is to provide thinner diapers. For example, U.S. Pat. No. 4,673,402 describes an absorbent article with a dual layer core where the lower core component has a relatively high concentration of superabsorbent material and a relatively high density. U.S. Pat. No. 5,102,597 describes absorbent polymeric macrostructures that comprise an interparticle crosslinked aggregate where individual superabsorbent particles are reacted with an interparticle crosslinking agent to form an aggregate which may take a sheet form. U.S. Pat. No. 5,411,497 discloses an absorbent article which includes superabsorbent material located in discrete pockets formed between a first and a second carrier layer and water-sensitive attaching means for securing the carrier layers together to form the pockets. U.S. patent application Ser. No. 10/776,839 discusses absorbent articles with a discontinuous layer of absorbent polymer material. The layer may contain up to 20% of an absorbent fibrous material.

The art has also considered improvement to the absorbent polymer materials that are a component of modern diaper cores by improving the capacity and/or permeability thereof. The hydrogel forming absorbent polymer disclosed in U.S. Pat. No. 5,599,335 has a Performance Under Pressure capacity of at least about 23 g/g and a Saline Flow Conductivity of at least about $30 \times 10^{-7}$ ($cm^3$ seconds)/g. U.S. Pat. No. 6,710,225 describes superabsorbent materials with a Modified Absorbency Under Load value of not less than about 20 g/g and a Tau value (time to reach 60% of equilibrium absorption capacity) of not less than 0.8 min.

Absorbent structures comprising differing superabsorbent materials are also discussed. European Pat. No. 401 189 B2 discusses absorbent articles with two separate layers made up of different superabsorbents; one of the superabsorbents has a high absorption rate, the other superabsorbent has a high liquid retention rate under pressure. The superabsorbent layers are separated by one or more distance maintaining layers. U.S. Pat. No. 5,728,082 describes a first fluff layer with a first superabsorbent material mixed thereinto, the first superabsorbent having a high degree of crosslinking, and a second layer which contains a second superabsorbent having a higher liquid absorbency than the first superabsorbent. U.S. Pat. No. 5,836,929 discusses absorbent articles with an upper layer that consists mainly of a first superabsorbent material with a Gel Layer Permeability value of at least about $4 \times 10^{-7}$ ($cm^3$ seconds)/g and a lower assembly with an Absorption Against Pressure of at least 15 g/g. The upper layer also has void space for storage and redistribution of liquid discharges.

The art also has recognized the need for softening structures comprising high levels of absorbent polymer material. For example, U.S. Pat. No. 5,868,724 teaches slitting structures such as those described in the aforementioned U.S. Pat. No. 5,102,597. However, a treatment of this type may result in breaking interparticulate crosslinks reducing the stability of the structure.

However, there is a continuing need for absorbent articles having improved thinness and softness that maintain the capability to acquire and store enough of the fluid deposited thereon so as to continue to provide desirable wearer skin dryness and satisfactory leakage performance. Caregivers and adult wearers of such absorbent articles desire improved discretion in order that a diaper is less visible under clothes or, in the case of an infant diaper, looks more like underwear. More conformable cores are desired in order to reduce the amount of material placed between a wearer's legs.

SUMMARY

The present invention is directed to an absorbent article, preferably a disposable absorbent article, such as a diaper. The diaper has a thin, conformable absorbent core where the core has at least two layers, both of which have a density greater than about 0.4 $g/cm^3$. The first layer is intended to provide storage for the majority of acquired fluids and comprises a first absorbent polymer material with an Absorbency Against Pressure (AAP) value of at least about 20 g/g. The second layer, which provides temporary capacity for the acquired fluid and permanent storage for at least a portion thereof, comprises a second absorbent polymer material which has a ratio of Wet Permeability to SFC of at least 1.5:1 with respect to the first absorbent polymer material.

DETAILED DESCRIPTION

The present invention is directed to an absorbent article, preferably a disposable absorbent article, such as an infant diaper or adult incontinence product.

As used herein, the following terms have the following meanings:

The terms "absorbent polymer material"; "superabsorbent polymer"; "SAP"; "absorbent gelling material" and "AGM" all refer to a polymeric material that is capable of absorbing at least about 5 times its weight of an aqueous fluid such as 0.9% saline as measured using the Centrifuge Retention Capacity test.

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like.

"Diaper" refers to an absorbent article generally worn by infants and incontinent persons about the lower torso.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

The terms "comprise," "comprising," and "comprises" specify the presence of what follows (e.g., a component) but do not preclude the presence of other features, elements, steps or components known to the art or disclosed herein.

A structure that is "substantially cellulose free" means that the structure comprises at least about 90% absorbent polymer material.

Figure 1:
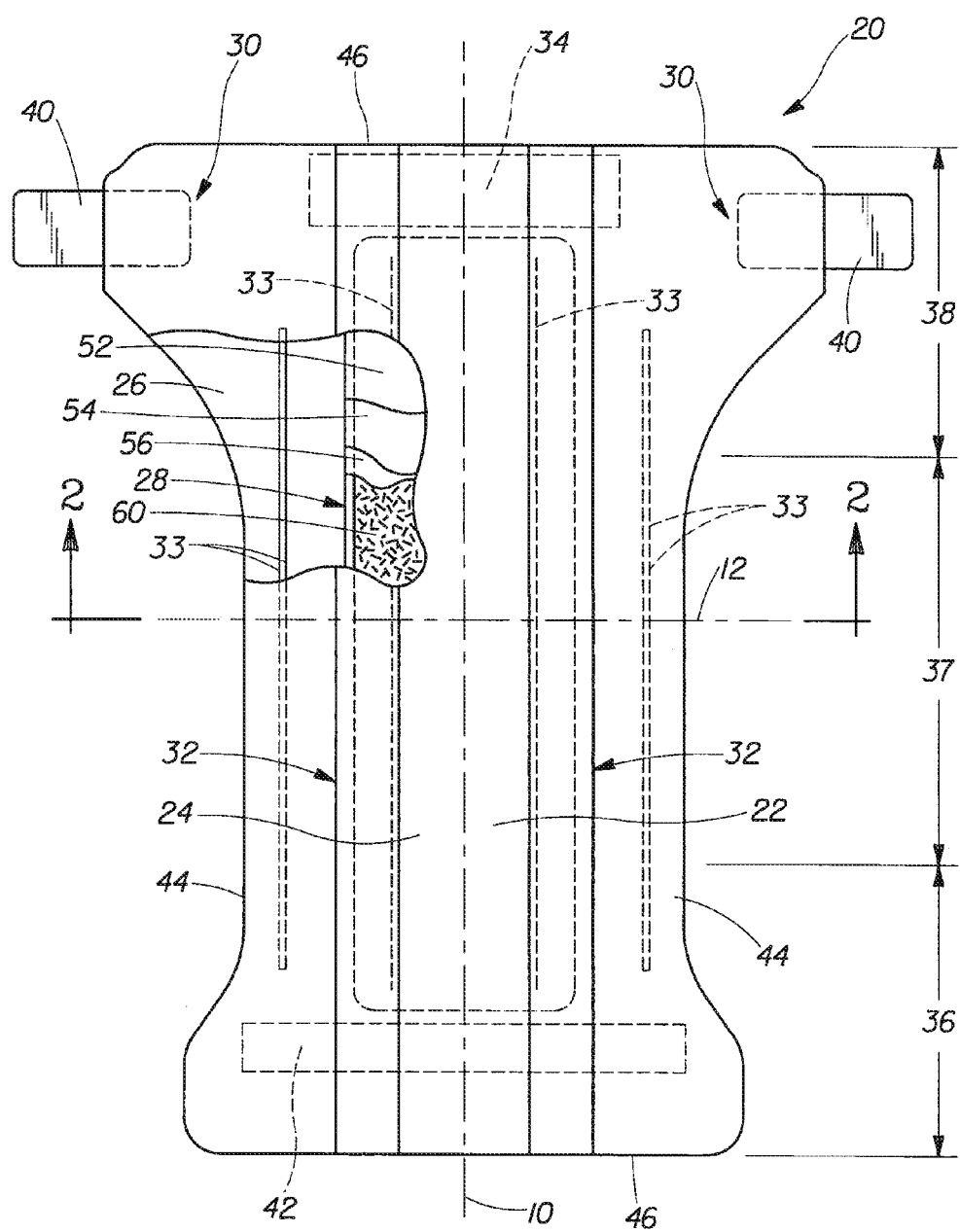
FIG. 1 is a plan view of a diaper as a preferred embodiment of an absorbent article according to the present invention.

FIG. 1 is a plan view of a preferred embodiment of an absorbent article according to the present invention diaper 20. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20 and does not include core 28 thereof. The chassis 22 comprises an outer covering including a liquid pervious topsheet 24 and/or a liquid impervious backsheet 26. The chassis preferably further includes side panels 30, elasticized leg cuffs 32, and elastic waist feature 34, the leg cuffs 32 and the elastic waist feature each typically comprise elastic members 33. One end portion of the diaper 20 is configured as a first waist region 36 of the diaper 20. The opposite end portion is configured as a second waist region 38 of the diaper 20. An intermediate portion of the diaper 20 is configured as a crotch region 37, which extends longitudinally between the first and second waist regions 36 and 38. The waist regions 36 and 38 may include elastic elements such that they gather about the waist of the wearer to provide improved fit and containment (e.g. elastic waist feature 34). The crotch region 37 is that portion of the diaper 20 which, when the diaper 20 is worn, is generally positioned between the wearer's legs. The diaper 20 is depicted with its longitudinal axis 10 and its transverse axis 12. The periphery of the diaper 20 is defined by the outer edges of the diaper 20 in which the longitudinal edges 44 run generally parallel to the longitudinal axis 10 of the diaper 20 and the end edges 46 run between the longitudinal edges 44 generally parallel to the transverse axis 12 of the diaper 20. The chassis also comprises a fastening system, which may include at least one fastening member 40 and at least one landing zone 42.

For unitary absorbent articles, the chassis 22 comprises the main structure of the diaper with other features added to form the composite diaper structure. While diaper 20 may be assembled in a variety of well-known configurations, preferred diaper configurations are described generally in U.S. Pat. No. 4,940,464, U.S. Pat. No. 5,554,145; U.S. Pat. No. 5,569,234; U.S. Pat. No. 6,004,306, U.S. patent application Ser. No. 10/171,249 and in U.S. patent application Ser. No. 10/824,121.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. Exemplary absorbent structures for use as the absorbent assemblies are described in U.S. Pat. Nos. 4,610,678; 4,834,735; 5,260,345; 5,387,207; 5,397,316; and 5,625,222.

Figure 2:
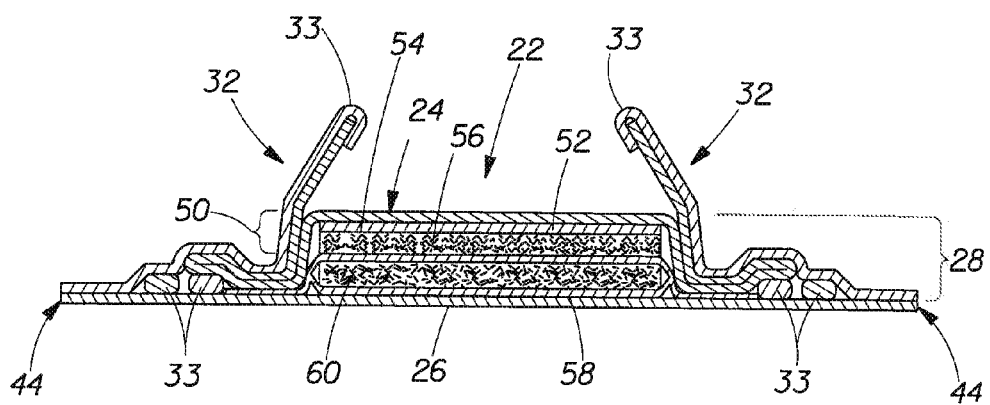
FIG. 2 is a cross-sectional view of the diaper shown in FIG. 1 taken along the sectional line 2-2 of FIG. 1.
Figure 3:
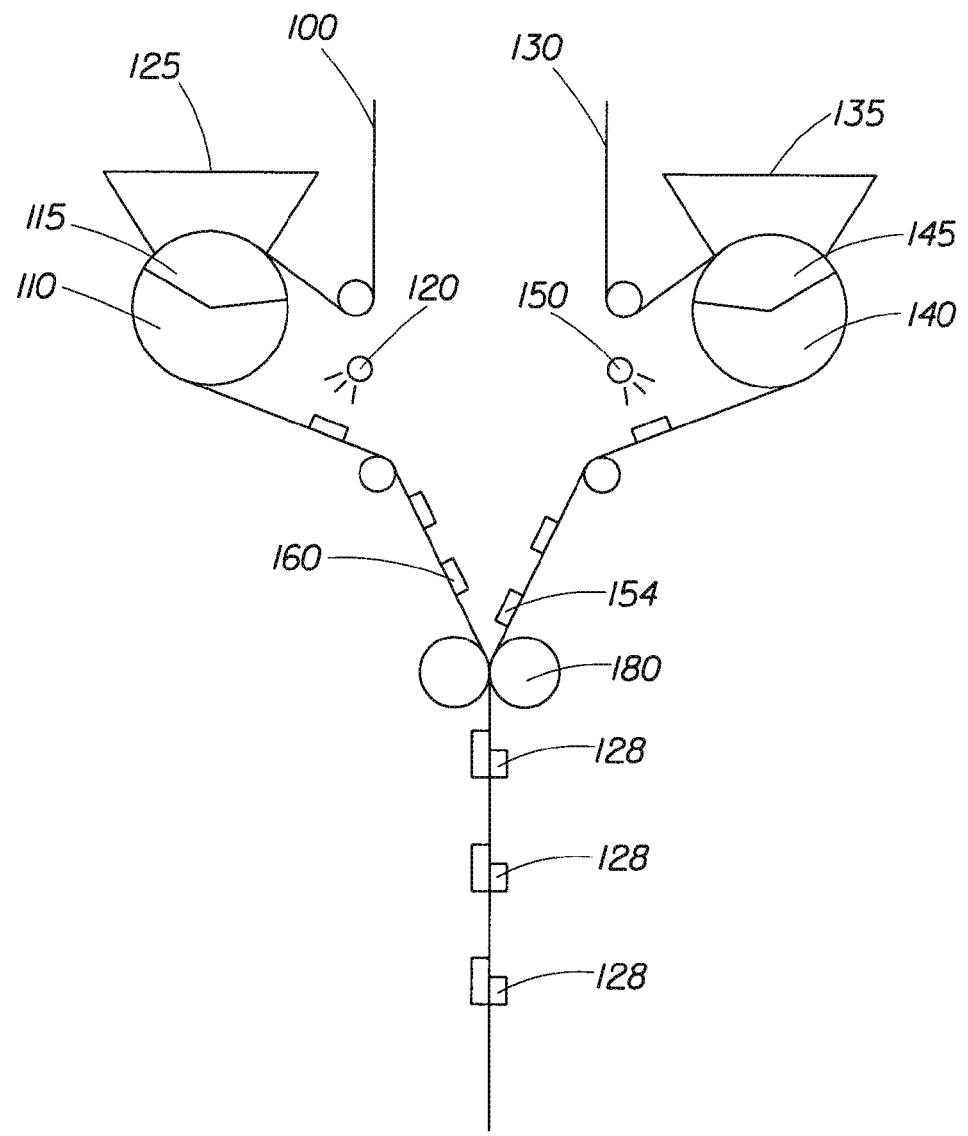
FIG. 3 is a schematic view of an apparatus for production of one preferred embodiment of the cores of the present invention.

As can be seen more clearly in FIG. 2, absorbent core 28 comprises at least two layers: acquisition system 50 which comprises at least acquisition/storage layer 54 that provides acquisition and temporary distribution and storage of acquired fluids and permanent storage of a portion thereof and storage layer 60 which provides the majority of the storage capacity of diaper 20.

The backsheet 26 is preferably joined with the topsheet 24 at least about a portion of the periphery thereof. The backsheet 26 prevents exudates absorbed by the absorbent core 28 and contained within diaper 20 from soiling other external articles that may contact the diaper 20, such as bed sheets and clothing. In preferred embodiments, the backsheet 26 is substantially impervious to liquids (e.g., urine) and comprises a laminate of a nonwoven and a thin plastic film such as a thermoplastic film having a thickness of about 0.012 mm to about 0.051 mm that has preferably been provided with micropores so as to be pervious to water vapor. Suitable backsheet films include those manufactured by Tredegar Industries Inc. of Terre Haute, Ind. and sold under the trade names X15306, X10962, and X10964.

The diaper 20 may also include such other features (not shown) as are known in the art including front and rear ear panels, waist cap features, elastics and the like to provide better fit, containment and aesthetic characteristics. Such additional features are well known in the art and are e.g., described in U.S. Pat. No. 3,860,003 and U.S. Pat. No. 5,151,092.

In order to keep the diaper 20 in place about the wearer, at least a portion of the first waist region 36 is attached by the fastening member 42 to at least a portion of the second waist region 38, so as to form leg opening(s) and a waist opening. The fastening system is designed to allow an article user to hold one element of the fastening system such as the fastening member 42, and connect the first waist region 36 to the second waist region 38 in at least two places. This is achieved through manipulation of bond strengths between the fastening device elements.

FIG. 2 shows a cross section of FIG. 1 taken along the sectional line 2-2 of FIG. 1. Starting from the body facing side, the diaper comprises the topsheet 24, the components of the absorbent core 28, and the backsheet 26. Absorbent core 28 preferably comprises an acquisition system 50, which comprises an acquisition layer 52 underlying topsheet 24 and acquisition/storage layer 54 disposed between acquisition layer 52 and the remaining component of core 28, storage layer 60.

In particularly preferred embodiments, core 28 is narrower in crotch region 37 than it is in either of waist regions 36, 38. Preferably, the ratio of the width of core 28 at transverse axis 12 to the widest lateral width thereof in either of first waist region 36 or second waist region 38 is less than 1.0. More preferably the ratio is less than about 0.8, most preferably less than about 0.7.

In one preferred embodiment acquisition layer 52 comprises a non-woven. Alternatively acquisition layer 52 may comprise a chemically stiffened, twisted and curled fibers, foams or other materials suitable for acquiring aqueous fluids as are known to the art. As will be discussed in greater detail below, acquisition/storage layer 54 is substantially free of cellulosic fibers and comprises a highly permeable superabsorbent material. Acquisition system 50 is disposed between storage layer 60 and topsheet 24.

Preferably, acquisition/storage layer 54 is in direct contact with storage layer 60. Alternatively, storage layer 60 may be wrapped by a core wrap material so as to dispose a layer between storage layer 60 and acquisition/storage layer 54. In one preferred embodiment the core wrap material comprises an upper wrap layer 56 and a lower wrap layer 58. The material comprising wrap layers 56, 58 preferably is a non-woven material. One preferred material comprises a spunbonded, a melt-blown and a further spunbonded layer (i.e. an SMS material). The non-woven materials are suitably made using synthetic fibers, such as polyethylene, polyester and most preferably polypropylene. Highly preferred are permanently hydrophilic non-wovens, and in particular nonwovens with durably hydrophilic coatings. Such hydrophilicity may be provided by surfactant treatment of the nonwoven. An alternative material comprises an SMMS-structure or a cellulosic tissue structure.

Similarly but not shown, acquisition/storage layer 54 may be provided with a wrap material so as to enclose the layer. Materials suitable for upper and lower wrap layers 56, 58 are also suitable for use as a wrap material in designs for core 28 where it is desired to wrap acquisition/storage layer 54.

In a third alternative, wrap materials 56, 58 enclose both acquisition/storage layer 54 and storage layer 60. In this embodiment acquisition/storage layer 54 and storage layer 60 are in direct facing contact.

Suitably, acquisition/storage layer 54 has the same dimensions as storage layer 60. Preferably, acquisition/storage layer 54 is laterally centered on storage layer 60 with the same lateral width but a shorter longitudinal length than storage layer 60. Acquisition/storage layer 54 may also be narrower than storage layer 60 while remaining centered thereon. Said another way, acquisition/storage layer 54 suitably has an area ratio with respect to storage layer 60 of 1.0. Preferably, the area ratio is less than 1.0 (e.g. less than about 0.75), more preferably less than about 0.50.

When the acquisition/storage layer 54 is longitudinally shorter than the storage layer 60, it is positioned such that more than 50% of its longitudinal length is forward of transverse axis 12. This positioning is desirable so as to place acquisition/storage layer under the point where urine is most likely to first contact diaper 20 (Sometimes called the "pee point"). Such positioning will facilitate acquisition of liquids absorbed by acquisition/storage layer 54.

Also, both acquisition/storage layer 54 and storage layer 60 may comprise an uneven distribution of absorbent polymer material basis weight in one or both of the machine and cross directions. Such uneven basis weight distribution may be advantageously applied in order to provide extra, predetermined, localized absorbent capacity to diaper 20. For example, the basis weight of absorbent polymer material in one or both of acquisition/storage layer 54 and storage layer 60 could be increased in the region of core 28 adjacent the "pee point".

A particularly preferred storage layer 60 is described in aforementioned U.S. patent application Ser. No. 10/776,839. In summary, the layer comprises an absorbent polymer material that is stabilized by a fibrous layer of thermoplastic adhesive to provide dry and wet immobilization of the absorbent polymer material. As can be seen, such a structure is substantially free of cellulosic fibers. A particularly preferred absorbent polymer material has an AAP of at least about 20 g/g and a Saline Flow Conductivity (SFC) that is greater than about $30 \times 10^{-7}$ (cm$^3$ seconds)/g. Preferably, AAP is greater than about 23 g/g, more preferably greater than about 25 g/g. AAP is measured according to the method described in the TEST METHODS section below and SFC is measured according to the method described in U.S. Pat. No. 5,599,335. These absorbent polymer materials are used at a basis weight of at least about 200 g/m$^2$, preferably at least about 400 g/m$^2$, more preferably at least about 600 g/m$^2$, to produce storage layer 60. In order to maintain satisfactory flexibility, the basis weight is also less than about 2000 g/m$^2$.

Because storage layer 60 is substantially free of cellulosic fibers, it has a higher density than components of an absorbent core used by the prior art for similar purposes. Suitably, a storage layer 60 according to the present invention has a density greater than about 0.4 g/cm$^3$. Preferably, the density is greater than about 0.5 g/cm$^3$, more preferably greater than about 0.6 g/cm$^3$.

Acquisition/storage layer 54 cooperates with the storage layer 60 to make more efficient use of the capacity thereof by providing temporary capillary storage of acquired fluids to allow time for fluid distribution into storage layer 60. In addition, because acquisition/storage layer 54 comprises an absorbent polymer material, it provides at least a portion of the ultimate storage capacity of absorbent core 28.

Importantly, because acquisition/storage layer 54 is intended to provide at least some temporary capillary storage and distribution of acquired fluid, it has a more open structure when wet than storage layer 60 (i.e. the wet porosity is greater). The art has typically used fibrous structures (e.g. blends of cellulose fluff and superabsorbent material or crosslinked cellulose fibers for this purpose). However, such fibrous structures have considerable dry bulk compared to the substantially cellulosic fiber free acquisition/storage layers 54 of the present invention. One measure of wet porosity is Wet Permeability. Thus, a suitable absorbent polymer material for use in the acquisition/storage layer 54 has an Wet Permeability that is higher than the SFC of the absorbent polymer material that is used in the storage layer 60. Preferably the Wet Permeability of the absorbent polymer material in the acquisition/storage layer 54 is at least about 1.5 times the SFC of the absorbent polymer material used in the storage layer 60, more preferably the Wet Permeability of the absorbent polymer material in the acquisition/storage layer 54 is at least about 3 times the SFC of the absorbent polymer material used in the storage layer 60, still more preferably 5 times. A particularly preferred absorbent polymer material for use in the acquisition/storage layer 54 has a Wet Permeability that is at least about 7.5 times the SFC of the absorbent polymer material that is used in storage layer 60.

Suitably, the absorbent polymer material that is used in acquisition/storage layer 54 has a Wet Permeability of at least about $400 \times 10^{-7}$ (cm$^3$ seconds)/g. Preferably, the material for acquisition/storage layer 54 has a Wet Permeability of at least about $600 \times 10^{-7}$ (cm$^3$ seconds)/g, more preferably at least about $800 \times 10^{-7}$ (cm$^3$ seconds)/g and still more preferably at least about $1000 \times 10^{-7}$ (cm$^3$ seconds)/g.

These absorbent polymer materials are used at a basis weight of at least about 100 g/m², preferably at least about 250 g/m², more preferably at least about 400 g/m², to produce acquisition/storage layer 54.

Because an acquisition/storage layer 54 according to the present invention is substantially free of cellulosic fibers, it has a higher density than components of an absorbent core used by the prior art for similar purposes. Suitably, an acquisition/storage layer 54 according to the present invention has a density greater than about 0.4 g/cm³. Preferably, the density is greater than about 0.5 g/cm³, more preferably greater than about 0.6 g/cm³.

Ideally, an absorbent polymer material suitable for the acquisition/storage layer 54 also can swell rapidly on exposure to an aqueous fluid. Such rapid swelling, combined with the high Wet Permeability provides capillary volume for acquisition and temporary storage of such aqueous fluids. Such interstitial void volume is typically at least about 15 ml of absorbent polymer material, preferably at least about 25 ml, more preferably at least about 30 ml. Suitably, an absorbent polymer material should have a free swell rate as measured according to the method described in the TEST METHODS section below of at least about 0.1 g/g/sec, preferably greater than about 0.2 g/g/sec, more preferably greater than about 0.3 g/g/sec.

In addition to providing temporary storage, acquisition/storage layer 54 also provides "permanent" storage for at least a portion of fluid acquired by diaper 20. As such, the absorbent polymer material therein has some capacity for such storage. Suitably, the absorbent polymer material has a CRC of at least about 5 g/g, preferably greater than about 9 g/g, more preferably greater than about 11 g/g. However, in order to provide the needed permeability, the CRC of an absorbent polymer material suitable for use in the acquisition/storage layer 54 is less than about 20 g/g. A particularly preferred absorbent polymer material for use in the acquisition/storage layer 54 has a CRC of between about 9 g/g and about 18 g/g.

As will be recognized, this "permanent storage" is a fraction of the full capacity of core 28 because of the relatively low value for CRC. Typically, acquisition/storage layer 54 comprises less than about 25% of the overall capacity of core 28. In some designs acquisition/storage layer 54 comprises less than about 20% of the overall capacity or even less than about 15%. However, this capacity is important because the bulk of the fluid stored therein, after equilibration with storage layer 60, is stored via an osmotic process (i.e. such fluid is stored in the same manner as fluid is stored in the storage core 60) so this storage is truly "permanent". Said another way, the applied pressure required for such a layer to "give up" osmotically stored fluid is greater than pressures typically encountered during wear. Since the diaper designs of the present invention intentionally provide that acquisition/storage layer 54 contributes a portion of the needed permanent storage, acquisition storage layer 54 suitably comprises at least about 5%, preferably at least about 10%, of the capacity of core 28.

Absorbent polymer materials suitable for use in an acquisition/storage layer 54 are further described in the aforementioned U.S. patent application Ser. No. 10/950,011 entitled "Absorbent Articles Comprising Superabsorbent Polymer Having a Substantially Non-covalently Bonded Surface Coating" filed in the name of Beruda, et al. on Sep. 24, 2004, in U.S. patent application Ser. No. 10/941,672 entitled "Absorbent Articles Comprising Fluid Acquisition Zones with Superabsorbent" filed in the name of Beruda, et al. on Sep. 15, 2004 and in JP 2004-105118, entitled "An Aqueous-Liquid-Absorbing Agent and Its Production Process", filed in the name of Nippon Shokubai Co. Ltd. on Mar. 31, 2004.

Acquisition/storage layer 54 and storage layer 60 also cooperate to provide diaper 20 with improved wearer fit and comfort. Specifically a diaper 20 that comprises a core 28 where the acquisition system 50 includes at least an acquisition/storage layer 54 according to the present invention has desirable low caliper and crotch softness. As will be recognized, a low caliper and a soft material result in a flexible core that can more closely conform to a wearer's body throughout the full range of wearer motion. Such thin/soft diapers are also less visible under a wearer's clothing and can have a very underwear-like appearance.

As noted above, cores 28 according to the present invention have a desirable low caliper. Desirably, the acquisition system 50 of the present invention comprises both an acquisition layer 52 and an acquisition/storage layer 54. For a core 28 of this construction dry core caliper is less than about 5 mm when measured at the center of acquisition layer 52. Preferably, the caliper of core 28 is less than about 4.5 mm, more preferably less than about 4 mm when measured at the center of acquisition layer 52. Structures that do not incorporate the acquisition layer 52 are even thinner.

The combination of wet porosity and permanent storage capacity provided by acquisition/storage layer 54 provides the aforementioned caliper reduction because bulky structure of the prior art is replaced therewith. As a result, the portion of core 28 in the crotch region 37 that comprises substantially only absorbent polymer material and any core wrap material attached thereto has a higher In Plane Radial Permeability than a similar portion of core 28 comprising substantially only absorbent polymer material and associated core wrap material from second waist region 38. Suitably, the ratio of In Plane Radial Permeability in crotch region 40 to In Plane Radial Permeability in second waist region 38 is at least about 1.5:1.0, preferably the ratio is greater than about 2.5:1.0, more preferably greater than about 3.0:1.0. A method for measurement of In Plane Radial Permeability is given in the TEST METHODS section below.

It should be noted that, when many of the absorbent structures of the art discuss caliper, the caliper of the absorbent structure is discussed in terms of only a single layer, rather than the assembled layers necessary to form a complete core 28 for a diaper 20. Thus it is believed the low caliper of a core 28 of the present invention is particularly advantageous. Said another way, the low caliper of core 28 provides diaper 20 with a desirable low caliper. That is, the thickness of all diaper components between the body surface of the topsheet and the garment surface of the backsheet is meaningfully less than the thickness of prior art diapers. For example, in one embodiment, a diaper 20 that comprises a core 28 according to the present invention has a caliper (measured at the center of acquisition layer 52) that is less than about 5 mm. Preferably, the caliper of diaper 20 is less than about 4 mm.

Core 28 according to the present invention is also desirably soft. Without being bound by theory, it is believed that the combination of a thin construction as discussed above (as is known, stiffness increases with thickness) and flexible joinder of the absorbent polymer particles by the fibrous thermoplastic adhesive cooperate to provide the desirable softness. As a result, core 28 can more readily conform to varying wearer body shapes and respond to wearer motion. For example, as discussed in Example 3, caregivers using an infant diaper having a core according to the present invention report that the diapers were thin soft and fit their babies better than a diaper according to the prior art.

The absorbent cores 28 of the present invention not only have the low caliper and improved softness discussed above they also provide a wearer with desirable fluid handling properties. Specifically, a core 28 of the present invention maintains the acquisition rate and absorbent capacity of cores according to the prior art while simultaneously providing substantially reduced dry caliper and improved softness.

Acquisition rate is important because, the longer aqueous fluids, such as urine, remain on the body surface of topsheet 24, the higher the risk of leakage that is not controlled by chassis components such as cuffs 32. Also, urine in direct contact with the skin increases the risk of skin health issues, such as diaper rash. The ability to rapidly acquire aqueous fluids when core 28 is partially saturated is particularly important because the fluid handling capability of core 28 is being stressed by previously acquired aqueous fluids so such fluids are more likely to remain on the body surface of topsheet 24. Said another way, a core 28 according the present invention can still rapidly acquire a meaningfully large gush of fluid while partially saturated from previously acquired gushes as described in the Acquisition Rate method below. Suitably, the fourth gush acquisition rate for a size 4 diaper using the absorbent member described herein is less than about 160 seconds for a 75 ml gush when measured using the method described in the TEST METHODS section below. Preferably, the acquisition rate is less than about 150 seconds, more preferably less than about 130 seconds. As noted above, such acquisition rates are comparable to the thicker absorbent cores of the prior art.

As is also known, the required absorbent capacity for an absorbent article is basically defined by the intended use thereof. That is, an absorbent article intended for adult incontinence uses will have a larger design capacity than an absorbent article intended for an infant. Importantly, an absorbent core 28 according to the present invention does not give up the capacity to store an appropriate quantity of aqueous fluid in order to provide a reduction in core caliper. One way of considering capacity is as normalized capacity, that is capacity per unit area. This approach takes into account that absorbent articles designed for larger wearers will have both a larger design capacity and a larger core area to absorb fluids deposited thereon. Suitably, a core 28 according to the present invention will have a normalized capacity in the portion thereof that comprises acquisition storage layer 54 of greater than about 0.5 g/cm$^2$. Preferably, the normalized capacity in the portion thereof that comprises acquisition storage layer 54 is greater than about 1.5 g/cm$^2$, more preferably greater than about 3.0 g/cm$^2$. In those portions of core 28 that do not comprise acquisition/storage layer 54 the normalized capacity is lower. For designs where the bulk of the capacity for aqueous liquids is within or adjacent to the crotch region 37, suitably, the normalized capacity in such areas is less than about 0.9 g/cm$^2$, preferably less than about 0.5 g/cm$^2$, more preferably less than about 0.2 g/cm$^2$. In some embodiments that are designed to provide a substantial portion of the ultimate storage for core 28 in one or both of waist regions 36, 38, such capacities may be higher, for example greater than about 0.9 g/cm$^2$, even greater than about 1.5 g/cm$^2$. As will be recognized, if it is desired to calculate the total capacity of a core 28, the respective areas of a core 28 with and without acquisition layer 54 can be determined using means known to the art (e.g. image analysis) and those areas multiplied by the normalized capacity for the area to determine the total capacity of a core 28 having a particular size.

Storage layer 60 can suitably be produced using the method described in the aforementioned U.S. patent application Ser. No. 10/776,839.

Acquisition/storage layer 54 can be produced using a method that is substantially the same as that used to produce storage layer 60. The main difference is that, rather than being provided with an uneven surface so as to provide areas of junction where an adhesive directly contacts a substrate layer as described in U.S. patent application Ser. No. 10/776,839, a laydown drum is provided with a series of "pockets" having a shape and volume substantially defined by the desired shape and volume of acquisition/storage layer 54. As will be recognized, the shape and volume of these pockets may be used to provide a predefined absorbent polymer material profile to one or both of acquisition/storage layer 54 and storage layer 60. This laydown drum is provided with vacuum means as described in the aforementioned U.S. patent application Ser. No. 10/776,839 that is suitable for drawing a substrate into the pocket. Any nonwoven suitable for use as a substrate for storage layer 60 is also suitable for use to produce acquisition/storage layer 54.

In one preferred embodiment, storage layer 60 and acquisition/storage layer 54 are produced so as to provide a core 28 with no upper wrap layer 56 therebetween. One suitable process for producing this structure is shown in FIG. 4 and discussed in the following paragraphs.

Figure 4:
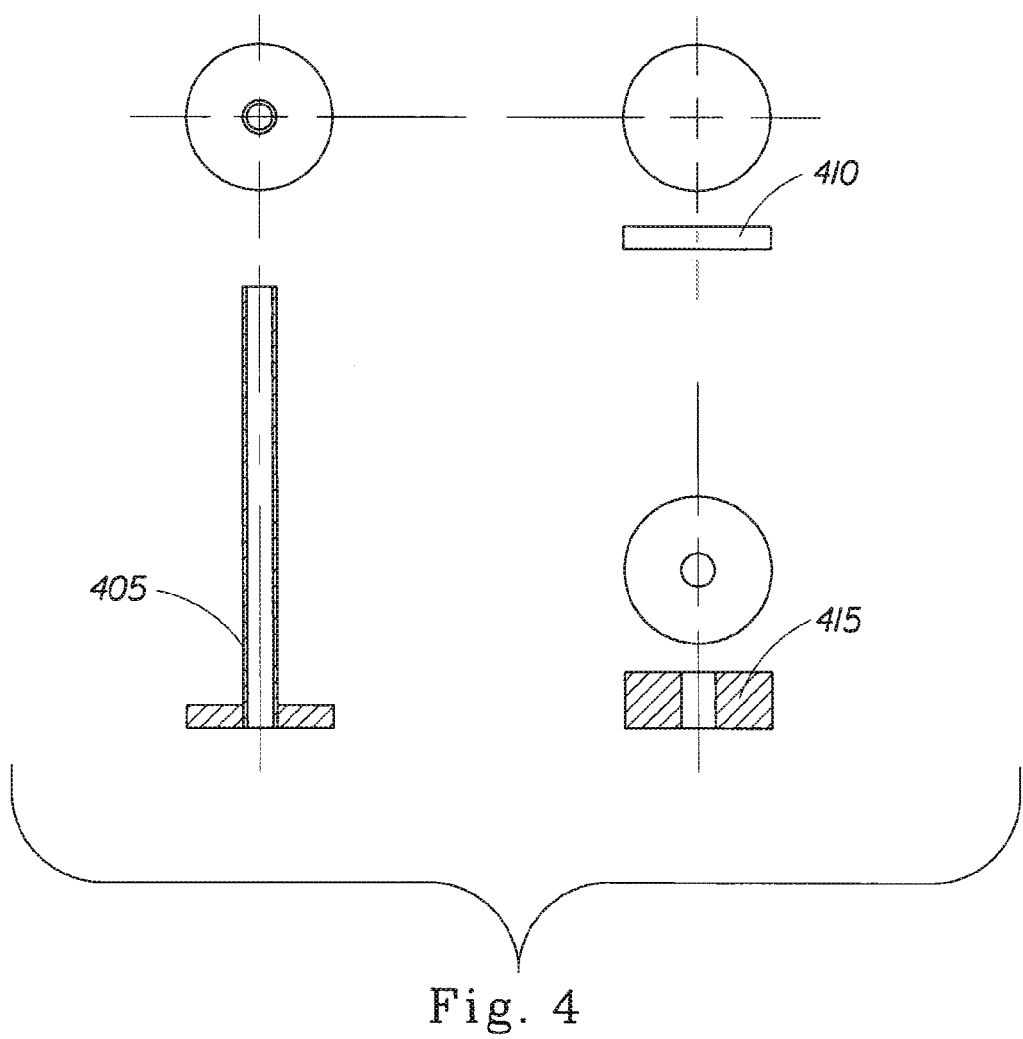
FIG. 4 is a schematic view of a portion of an apparatus for measuring In Plane Radial Permeability.

As can be seen in FIG. 4, a storage layer precursor 160 can be produced by depositing first absorbent polymer material (not shown) that is contained in hopper 105 onto substrate 100. As described in U.S. patent application Ser. No. 10/776, 839, first substrate 100 is caused to conform to depressions (not shown) in first laydown drum 110 by a vacuum in first vacuum portion 115 so as to enable filling the depressions with the first absorbent polymer material as the depression passes under first hopper 105. After the depression passes under first hopper 105 the first absorbent polymer material is stabilized with a thermoplastic polymer applied at first spray station 120 so as to form storage layer precursor 160.

Acquisition/storage layer precursor 154 can be produced in essentially the same manner. Second substrate 130 is caused to conform to a depression in second laydown drum 140 prior to filling with a second absorbent polymer (not shown) delivered from second hopper 135. The second absorbent polymer material in the filled depressions is stabilized by thermoplastic polymer delivered from second spray station 150.

To form core precursors 128, the substrate webs carrying storage layer precursor 160 and acquisition/storage layer precursor 154 are phased for proper alignment using methods known to the art and combined at nip 180. As will be recognized, the rolls comprising nip 180 can be provided with pockets to receive precursors 160, 154 to enable the first and second substrates 100, 130 to be sealed about the periphery of storage layer precursor 160 effectively enclosing core precursor 128 in a wrap material. If necessary, one or both of the rolls comprising nip 180 could be heated to soften the thermoplastic material to facilitate the enclosure step.

As will also be recognized separate nips (not shown) essentially the same as nip 180 and a web of a suitable nonwoven material (not shown) could be provided between the spray stations 120, 150 and nip 180 if it was desired to enclose either or both of precursors 160, 154.

TEST METHODS

Absorbency Against Pressure (AAP)

Absorbency Against Pressure is suitably measured according to the method described in U.S. Pat. No. 6,232,520 with the following exceptions:

1. A saline solution (0.9%) is used instead of the test fluid described in U.S. Pat. No. 6,232,520. The saline solution may be prepared according to the description provided below for the Free Swell Rate test.
2. A confining pressure of 0.7 psi (4.8 kPa) is used.

Basis Weight

European Disposables and Nonwovens Association (EDANA) standard method for Mass per Unit Area (40.3-90) is suitable.

Caliper

European Disposables and Nonwovens Association (EDANA) standard method for Thickness (No 30.5-99) is suitable. A suitable apparatus is described in paragraph 4.1. The specified pressure is 2.1 kPa.

Centrifuge Retention Capacity

European Disposables and Nonwovens Association (EDANA) standard method 441.2-02 is suitable.

Density

Density is defined as Basis Weight divided by Caliper.

Fluid Acquisition

The fluid acquisition test provides a measure of the ability of an absorbent structure to rapidly acquire aqueous fluids under simulated use conditions. The sample is loaded with a 75 ml/gush of 0.9% saline solution at a rate of 15 ml s$^{-1}$ using a pump (The Model 7520-00 available from Cole Parmer Instruments Co. of Chicago, Ill. is suitable). The time to absorb saline solution is recorded by a timer. The gush is repeated at 5 minute gush intervals for 4 gushes.

The test sample, which comprises a core and includes a topsheet and a backsheet, is arranged to lie flat on a foam platform within a polymethyl methacrylate (e.g. PERSPEX) box (see the detail assembly of the test apparatus in U.S. Pat. No. 6,083,210). The method as described herein is suitable for absorbent structures with an ultimate storage capacity of about 300 ml to about 400 ml (size 3). If products with significantly different capacities are evaluated (such as can be envisaged for adult incontinence products or diapers for premature infants), the settings in particular the fluid volume per gush should be adjusted appropriately to about 20% of the total article design capacity and the weight for the confining pressure should be adjusted to be representative of the confining pressure of a wearer. Any deviation from the standard test protocol should be recorded. The following provides suitable setup parameters for various sizes of infant diapers.

| Size | Loading Volume (ml) | Loading Rate (ml/sec) | Weight (kg) |
| --- | --- | --- | --- |
| Newborn | 16 | 5.33 | 0.9 at each end of plate = 1.8 total |
| 1 | 24 | 8 | 2.3 at each end of plate = 4.6 total |
| 2 | 40 | 8 | 2.9 at each end of plate = 5.8 total |
| 3 | 50 | 10 | 4.5 at each end of plate = 9.0 total |
| 4 | 75 | 15 | 9.1 at each end of plate = 18.2 total |
| 5 | 75 | 15 | 9.1 at each end of plate = 18.2 total |

The outer surface of the backsheet faces the foam platform. A PERSPEX plate with a 5 cm diameter opening substantially in its middle is placed on top of the sample. The sample is oriented such that the topsheet is directly below the opening of the PERSPEX plate, The opening in the plate (i.e. the loading point for the saline solution) is placed about 10 cm from the front edge of the complete core and about in the halfway between the lateral sides of the core. Saline solution is introduced to the sample through the cylinder fitted and glued into the opening. Electrodes are about 1 mm to 2 mm above the surface of the absorbent structure and also connected to the timer. Loads are placed on top of the plate to simulate, for example a baby's weight. Two 4.5 kg weights are placed on top of the plate with an area of 744.6 cm$^2$ (51 cm×14.6 cm).

As saline solution is introduced into the cylinder. It builds up on top of the absorbent structure thereby completing an electrical circuit between the electrodes. This starts the timer. The timer is stopped and recorded when the absorbent structure has absorbed the gush, and the electrical contact between the electrodes is broken.

Acquisition rate is defined as the time in seconds required to absorb the gush volume that is delivered. The acquisition rate is calculated for each gush introduced into the sample.

Free Swell Rate (FSR)

This method is suitable for measurement of the swelling rate of an absorbent polymer material in a 0.9% saline solution. The amount of time taken to absorb a predefined quantity of fluid without stirring or providing a confining pressure is recorded and reported in grams of fluid (0.9% saline) absorbed per gram of polymer particles per second, e.g. g/g/sec).

The saline solution is prepared by adding 9.0 gram of NaCl into 1000 ml distilled, deionized water and stirring until all NaCl is dissolved.

The sample amount (Determined according to the equation below) is weighed (to an accuracy of ±0.0001 g) and spread evenly over the bottom of a tared 25 ml beaker.

$w_{dry}$=dry weight [g]=20 [g]/(0.75×$CRC$ [g/g])

Then 20 g of the saline solution (at 23° C.±1° C.) is added quickly to the beaker with the sample and the timer is started as soon as the liquid touches the sample. The filled beaker is weighed to an accuracy of ±0.01 g to determine the weight of saline solution added ($w_{liq}$) by subtracting the tare weight of the beaker and $w_{dry}$ from the weight of the filled beaker.

When the last part of the undisturbed fluid surface meets the swelling sample, e.g. judged by a change in light reflection from the fluid surface, the time $t_s$ is recorded.

The test is repeated twice more, to obtain 3 values.

The Free Swell Rate is then calculated for each replicate and averaged to obtain the Free Swell Rate in g/g/sec.

$FSR=w_{liq}/(w_{dry}×t_s)$

In Plane Radial Permeability (IPRP)

This test is suitable for measurement of In Plane Radial Permeability (IPRP) of absorbent structures. The structure is swollen under pressure in a saline solution (0.9% NaCl). Flow rate is determined by measuring the quantity of solution flowing through the structure in a substantially horizontal-plane as a function of time. (Reference: J. D. Lindsay, "The Anisotropic Permeability of Paper" TAPPI Journal, (May 1990) pp 223) Darcy's law and steady-state flow methods are used for determining in-plane saline flow conductivity.

Equipment

The equipment and chemicals specified in the below sections are described in details for properties, dimensions and suggested suppliers (Mettler-Toledo; Sigma-Aldrich). Unless otherwise indicated, alternate sources of equivalent chemicals and equipment may be used, provided they meet or exceed the requirements necessary to preserve the accuracy and precision of the method.

Figure 5:
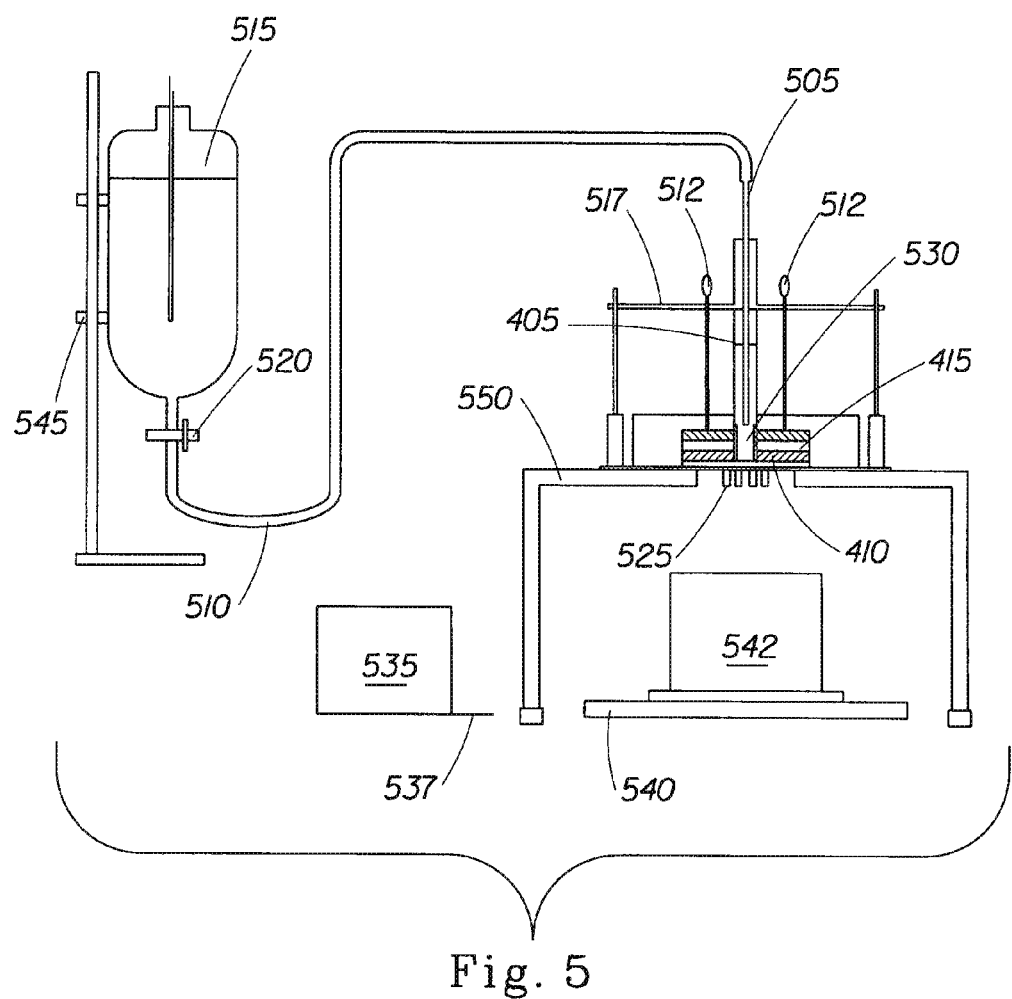
FIG. 5 is a schematic view of an apparatus for measuring In Plane Radial Permeability.

In Plane Radial Permeability See FIGS. 4 and 5 and Discussion Below

Apparatus

| | | |
|---|---|---|
| Pneumatic sample cutter (die cutter) | Catalog No. 240-10 available from Thwing Albert Instrument Co. of Philadelphia, PA | |
| Die cutter Shape | Circular (donut shape) I.D. 12 mm; E.D. 70 mm | |
| Personal Computer | Minimum Pentium III with 128 Mb RAM and data acquisition software able to capture weight data as a function of time. | |
| Balance Data Link (computer interface) | Mettler-Toledo (or equivalent) | |
| Analytical Balance (±0.001 g) | Mettler-Toledo PR203 (or equivalent) | |
| Balance (±0.01 g) | Mettler-Toledo PR2002 (or equivalent) | |
| Caliper Measurement Device (±0.01 mm) | Mitutoyo 575-123 (or equivalent) | |
| Volumetric Flask | 2000 ml | Z30,657-6 (or equivalent) |
| Separatory Funnel | 1000 ml | Z30,430-1 (or equivalent) |
| Cone/Screw-thread Adapters | | Z30,233-3 (or equivalent) |
| Air/Steam Inlet Tube | | Z30,475-1 (or equivalent) |
| Support Stand | | Z19,035-7 (or equivalent) |
| Stainless Steel Clamp | | Z17,728-8 (or equivalent) |
| Clamp Holder | | Z12,182-7 (or equivalent) |
| TYGON Tube | I.D. 8 mm; O.D. 11 mm | Z27,985-4 (or equivalent) |
| Rigid Plastic Tube | I.D. 6 mm; O.D. 9 mm | Commercially available |
| Timer(60 minutes capability) | | Z26,612-4 (or equivalent) |
| Beaker | 800 ml | Z23,188-6 (or equivalent) |
| Reagents and Chemicals | | |
| Distilled Water | <0.01 µS house supply or commercially available | |
| Sodium Chloride | >99% ACS Reagent S 9888 (or equivalent) | |
| Saline Solution 0.9% | See the Free Swell Rate test method | |

Test Procedure

Equipment Set Up

1. The IPRP sample holder is shown in FIG. 4 and comprises PLEXIGLAS bottom plate 410, plunger 405, cylindrical stainless weight 415, central cylindrical mesh 530 (diameter=12 mm; height=60 mm, a suitable material is available form Weisse & Eschrich of Ludwigsstadt, Germany as Catalog No. 1.4401). Plunger 405 comprises an annular PLEXIGLAS base plate (od=70 mm; id=12 mm) with a PLEXIGLAS tube of 165 mm length fixed at the center thereof. The total weight of plunger and the stainless steel weight should be 788 g (+8 g) to provide 2.1 kPa confining pressured during the measurement.
2. Measure and clearly mark the plunger tube at a height of 100 mm (±0.5 mm) starting from the bottom side of base plate with a permanent marker. This is the reference for the fluid level to be maintained during the analysis. *Maintenance of correct, constant fluid level (hydrostatic pressure) is critical to the analysis.* Suitable methods are described in Chatterjee, P. K. and Gupta, B. S., eds., "Absorbent Technology", 2002 Elsevier, New York.
3. Position the balance 540 under the IPRP stand 550 aligning the weight pan to the center of the stand 550. Ensure that the stand 550 is perfectly flat and level to avoid bias in any direction of fluid penetration. Position the collection container 542 onto the balance 540 pan aligned with the four tubes 525 present under the IPRP stand 550 to allow the liquid to drop into them.
4. Using the clamp and the clamp holder 545 fix the separatory funnel to the stand to have the stopcock at the same level as the four tubes present in the bottom of IPRP stand. Insert and hold the inlet tube in the adaptor and position it on top of the funnel. Connect the TYGON tube (~1000 mm) to the stopcock of the funmnel and the plastic rigid tube (~200 mm) at the end of the TYGON tube being sure that it is long enough to load fluid into the plunger tube. Fill the funnel with a 0.9% saline solution.
5. Center the plunger 405 on the bottom plate 410 and put them in the stand 550. Mark with a permanent marker the relative position of the plunger 405 and bottom plate 410 with respect to the support 550 and set the caliper gauge 512 to zero.
6. Connect the digital output of the balance to the personal computer where previously has been installed the data acquisition software.

Sample Preparation

Remove the topsheet and any fiber (nonwoven or cellulose) based acquisition layer from the complete diaper retaining all absorbent polymer material containing layers. The backsheet can be retained to avoid further disintegration of the total absorbent member. Use die cutter to cut the sample at each location in a donut shape having 700 mm—$R_o$ exterior diameter and 12 mm—$R_i$ interior diameter. Cut out samples from the crotch region and the rear back waist area of the diaper as described in the Normalized Core Capacity test method herein.

Measurement

1. Disassemble the pre set plunger from bottom plate.
2. Carefully insert the bottom plate 410 in the stand support 550. Place the sample onto the bottom plate 410 using the central cylindrical mesh 530 as a positioning reference. Position and center the plunger 405 and stainless steel weight 415 on the sample. Plunger 405 should not touch any side structure and move without resistance in the vertical direction. Measure and record the dry sample caliper value using the gauge 412 display to an accuracy of 0.01 mm.
3. Position the glass straw 505, connected at the end of the tube 510 coming from the reservoir 515, in the center of the plunger 405 inlet tube making sure that the tip is below the 10 cm level. Use two clamps 517 to fix the straw in a way that it is not in touch with the inlet tube during the whole test.
4. Open the valve 520 connecting the reservoir with the inlet straw 505 and let the liquid flow trough the sample for pre-swelling for 30 minutes making sure that the liquid column is 10 (±0.1 cm) high.
5. Visually check that the liquid flux from each of the four flushing tubes in the sample holder are almost identical. Once an even flux distribution is reached go to the next step.
6. Measure and record the wet sample caliper using the gauge 512 display to an accuracy of 0.01 mm.—$L_1$ 7. Start the data acquisition software and acquire and store weight data from balance 540 on computer 535 as a function of time (insuring interface connection 537 is functioning properly). Data will be acquired for 5 minutes at 10 seconds interval.
8. During all test execution the liquid level into the plunger cylinder (10 cm±0.1 cm hydrostatic pressure) must be visually kept under control. In case the level is not correct it must be regulated by moving the inlet tube of reservoir 515.
9. When the acquisition of data is finished, close the stopcock and measure the final wet sample caliper value—$L_2$ using caliper gage 512 display to an accuracy of 0.01 mm. The difference from initial ($L_1$) and final caliper ($L_2$) is should not be bigger than 10%.
10. Remove the reservoir tube from the plunger. Carefully remove the plunger then wash and dry the whole sample holder.
11. Repeat the IPRP test minimum three times for each sample.

Calculation

The data collected should be in the form of grams of saline as a function of time recorded at 10 seconds interval. The data from 20 seconds to the end of the experiment should be used in the following calculations (the data collected prior to 20 seconds should not to be included in the calculation). Table 1 below contains an example of the calculations required for this method. Column 1 and Column 2 contain the time and fluid weight respectively, as collected by the data system. Column 3 contains the values of $Fs_{(t)}$ calculated at each time period after 20 seconds using Equation 1:

$$Fs_{(t)} = \frac{(g_{(i-1)} - g_{(i)})}{(t_{(i-1)} - t_{(i)})} \quad \text{(Equation 1)}$$

Column 4 contains the mid point of the time column calculated using Equation 2:

TABLE 1

$$t_{(1/2)} = \frac{(t_{(i-1)} + t_{(i)})}{2} \quad \text{(Equation 2)}$$

| Column 1<br>Time<br>(sec) | Column 2<br>Uptake<br>(g) | Column 3<br>$Fs_{(t)}$<br>(g/sec) | Column 4<br>$t_{(1/2)}$<br>(sec) |
|---|---|---|---|
| 0 | 0 | | |
| 10 | 33.28 | | |
| 20 | 66.42 | 3.314 | 15 |
| 30 | 99.98 | 3.356 | 25 |
| 40 | 133.37 | 3.339 | 35 |

Calculate the average of the individual flow rates. Record this average as $Q^1$ and use the value along with the following Equation 3 to calculate $k_r$ (cm²):

$$k_r = \frac{(Q^1/\rho_1) \cdot \mu \cdot \ln(R_0/R_i)}{2\pi \cdot Lp \cdot \Delta p} \quad \text{(Equation 3)}$$

Where:

$Q^1$ is the flow rate (g/s) obtained by extrapolating the slope and midpoint determined from regression analysis of the flow rate data from 20 seconds to 300 seconds.

$\rho_1$ is the liquid density; 1.01 g/cm³.
$\mu$ is the liquid viscosity at 20° C.; $10^{-3}$ Pascal seconds.
$R_0$ is the outer sample radius (mm).
$R_i$ is the inner sample radius (mm).
$Lp$ is the sample thickness (cm)
 [$Lp$ is the average before $L_1$ and after $L_2$ the flow measurement $L_p=(L_1+L_2)/2$] Where: $\Delta p$ is the pressure drop (Pa) calculated according to Equation 4:

$$\Delta p = (\Delta P + 0.5 L_p) \cdot g \cdot \rho_1 \cdot 10 \quad \text{(Equation 4)}$$

Where:

$\Delta P$ is the liquid hydrostatic pressure (cm).
g is the acceleration constant; 9.81 m/sec².
$\rho_1$ is the liquid density; 1.01 g/cm³.

Record the $k_r$ value and use it to calculate the In Plane Radial Permeability value Kr with the following Equation 5:

$$K_r = \frac{k_r}{\mu} \quad \text{(Equation 5)}$$

The IPRP value is expressed in $10^{-7}$ cm³ sec/g.

Reporting

Repeat the IPRP measurements for 3 replicates of each sample. For each replicate calculate the IPRP and report each IPRP value and the average thereof.

Normalized Core Capacity

This method is intended to determine the normalized core capacity in a predefined area of a fluid handling member. It is suitable for individual layers of such a fluid handling member or the entire member that comprises an assembly of such layers.

Sample Preparation

1) Open the side seals if the diaper is of the pants type. Remove all the elastics (leg cuffs, wait bands etc.) from the complete diaper and stretch to eliminate the folds of the diaper on the flat surface, facing the topsheet toward surface. If the fluid handling member is adhered to the backsheet do not attempt to separate it therefrom Take care to disturb the structure of the fluid handling member as little as possible
2) Mark the intersection of the longitudinal and transverse axes of the absorbent core (not the entire absorbent article—As will be recognized, the absorbent core may be placed asymmetrically with respect to the intersection of the longitudinal and transverse axes of the absorbent article).
3) To include any acquisition/storage component, cut a sample using a pneumatic cutter (A Catalog No. 240-10 available from Thwing Albert Instrument Co. of Philadelphia, Pa. is suitable) using a circular die having 60 mm diameter (This provides a defined surface area for the sample of 28.27 cm².) from the absorbent article centered on a position approximately 3 cm toward the diaper front waist edge of the marked intersection of core axes. For samples without an acquisition/storage component, cut the sample approximately 3 cm toward the marked intersection from the rear waist edge of the absorbent core.
4) Store the sample at 23° C.+1° C., 50%±2% RH for at least 24 hours prior to further evaluation. Conduct all testing under the same conditions.

Capacity Measurement

A confining pressure of 0.3 psi (2.1 kPa) is applied during the pre-swelling and throughout the measurement. The assembly used in the Wet Permeability test described below is suitable for holding the sample while the test is being conducted.

1) Prepare a 0.9% saline solution as described above.
2) Pour the solution into a large Petri dish having a surface area larger than the fluid handling member and a depth at least five times the caliper of the absorbent member. Pour enough of the saline solution into the Petri dish so as to insure that an excess of the saline solution is available for absorption.
3) Place the sample into the Wet Permeability assembly with the topsheet facing toward the bottom thereof and measure the total weight nearest 0.001 g. Record this weight as $w_2$
4) Put the Wet Permeability assembly and the sample therein onto a filter paper (e.g. No. 596, 90 mm diameter as is available from Schleicher & Schuell of Keene, N.H. or equivalent) that is submerged in the Petri-dish filled with saline solution.
5) Allow the sample to swell under a 0.3 psi (2.07 kPa) confining pressure for 60 minutes allowing the fluid handling member to become substantially saturated with the saline solution.
6) Remove the sample assembly from the saline and place it on a stack of 5 layers of paper hand-towels (Metsa Tissue (Helsinki, Finland), Katrin®, C-fold2) for 30 minutes to allow the free saline solution to drain under 0.3 psi confining pressure.
7) Weigh the saturated fluid handling member together with the sample assembly to the nearest 0.001 g. Record this weight as $w_3$
8) The capacity is defined as the saturated weight of the fluid handling member minus the dry weight of the fluid handling member under 0.3 psi confining pressure. ($w_3 - w_2$) and is reported in grams.

Calculation and Reporting

1) Repeat the surface area and capacity measurements for 3 replicates of each fluid handling member evaluated.
2) For each replicate calculate the normalized capacity by dividing the capacity measured for that replicate by the surface area, 28.27 cm² for that replicate.
3) Report each normalized capacity value and the average thereof.

Wet Permeability

Wet Permeability is suitably measured according to the method for Saline Flow Conductivity as is disclosed in U.S. patent application Ser. No. 10/950,011 entitled "Absorbent Articles Comprising Superabsorbent Polymer Having a Substantially Non-covalently Bonded Surface Coating" filed in the name of Beruda, et al. on Sep. 24, 2004.

EXAMPLES

Example 1

This example is intended to compare the fluid handling characteristics of a diaper according to the present invention with a diaper made according to U.S. patent application Ser. No. 10/776,851 both diapers had exactly the same construction with the exception of the material used for the acquisition/storage layer. The respective materials and the resulting core caliper and core fluid handling properties are shown in Table 1

TABLE 2

|  | Product of U.S. Pat. Application Ser. No. 10/776,851 | Product According to the Present Invention |
|---|---|---|
| Acquisition/storage Layer | Curly Cellulose Fibers (Basis Wt: 210 gram/m²) | Absorbent Polymer Material[1] (Basis Weight ~250 gram/m²) |
| Dry Caliper (mm) | 4.8 | 3.5 |
| Acquisition Rate (sec/15 ml) | | |
| 1st Gush | 37 (2) | 43 (1) |
| 2nd Gush | 62 (5) | 60 (3) |
| 3rd Gush | 95 (5) | 100 (6) |
| 4th Gush | 119 (7) | 125 (6) |
| Rewet[2] (mg) | 70 | 71 |

[1]PolyAcrylic Acid as is available from Nippon Shokubai KK of Himeji, Japan as QXL 1031
[2]Determined according to the method described in U.S. Pat. No. 6,085,579
As can be seen, the absorbent core of the present invention provides comparable fluid handling properties while being substantially thinner.

Example 2

This example is intended to compare the dry caliper of a diaper according to the present invention with commercially available diapers and a diaper made according to U.S. patent application Ser. No. 10/776,851. This comparison is shown in Table 2.

TABLE 3

| Product | Dry Caliper (mm) |
|---|---|
| Pampers ® Active Fit (size 4)[1] | 7.1 |
| Huggies ® Super-Flex (size 4)[2] | 7.2 |
| Huggies ® Pull-Ups ® Girl ®[3] | 3.2 |
| Huggies ® Pull-Ups ® Boy ®[3] | 4.0 |
| Product According to U.S. Patent Application Ser. No. 10/776,851[3] | 5.9 |
| Present Invention[4] | 3.9 |

[1]Available from Procter & Gamble GMBH of Schwalbach am Tanus, Germany
[2]Available from Kimberly Clark of Reigate, United Kingdom
[3]Available from Kimberly Clark of Neenah, WI
[4]Acquisition/storage layer consists of curly cellulosic fiber having a 250 g/m² basis weight
5. Acquisition/storage layer comprising polyacrylic acid as is available from of Nippon Shokubai KK of Himeji, Japan as QXL 1031

Example 3

This example compares the perceived thinness and softness of a diaper according to the present invention with a commercially available diaper. A group of babies weighing between 8 kg and 15 kg are identified. The caregivers for each of the babies are given 10 diapers each of:

a commercially available diaper (Pampers® Easy Ups size 4, as are available from Procter & Gamble of Schwalbach am Tanus, Germany) that was modified by a slight increase (~2 g) in the amount of absorbent polymer material; and a diaper having the same chassis as the commercially available product with a core according to the present invention.

The caregivers are instructed to use the test diapers instead of their usual product and to note how the diapers perform. Half of the caregivers are instructed to use the commercially available diaper first and half are instructed to use the diaper according to the present invention first.

After all of the diapers are used, each caregiver is asked to describe how what they noticed about the product they used.

The caregivers reported:
  Handling of bodily fluids (e.g. urine) is seen as comparable for the commercially available diaper and for the diaper having a core according to the present invention.
  Handling of bowel movements (i.e. feces) is seen as comparable for the commercially available diaper and for the diaper having a core according to the present invention.
  The diaper having the core according to the present invention is seen as thinner than the commercially available diaper both when dry and when wet.
  The diaper having a core according to the present invention is seen as having a better fit than the commercially available diaper.
  The diaper having a core according to the present invention is seen as being softer than the commercially available diaper.

Example 4

This example compares the normalized core capacity and the core caliper of a diaper according to the present invention and prior art diapers in the portion of the core where urine is most likely to first contact the core (I.e. the pee point"). All diapers tested were designed to be worn by a 8-15 kg infant.

TABLE 4

| Product | Core Caliper (mm) | Pee Point Normalized Core Capacity (g/cm$^2$) |
|---|---|---|
| Huggies ® Pull-Ups ® Girl ®[1] | 3.2 | 0.64 |
| Product According to U.S. Patent Application Ser. No. 10/776,851[2] | 5.0 | 1.93 |
| Present Invention[3] | 3.8 | 2.29 |

[1]Available from Kimberly Clark of Neenah, WI
[2]Acquisition/storage layer consists of curly cellulosic fiber having a 250 g/m$^2$ basis weight
[3]Acquisition/storage layer comprising polyacrylic acid as is available from of Nippon Shokubai KK of Himeji, Japan as QXL 1031

Example 5

This example is intended to compare the In Plane Radial Permeability of a single layer of an absorbent polymer material as described in U.S. Pat. No. 5,599,335 as is suitable for a storage layer according to the present invention with a dual layer structure where a layer comprising a high wet porosity absorbent polymer material according to the present invention is disposed on top of the layer comprising the absorbent polymer material as described in U.S. Pat. No. 5,599,335.

The layers were measured for In Plane Radial permeability (IPRP) according to the method described herein.

TABLE 5

| | IPRP ($10^{-7}$ cm$^3$ s/g) | |
|---|---|---|
| | A[1] | B[2] |
| Sample 1 | 135 | 461 |
| Sample 2 | 129 | 512 |
| Sample 3 | 138 | 356 |
| Average | 134 | 443 |

[1]Single layer comprising an absorbent polymer material according to U.S. Pat. No. 5,599,335.
[2]Dual layer structure according to the present invention comprising an absorbent polymer material according to U.S. Pat. No. 5,599,335 and a layer comprising a high wet porosity absorbent polymer material according to the present invention The IPRP ratio is 3.31.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While various embodiments and/or individual features of the present invention have been illustrated and described, it would be obvious to those skilled in the art that various other changes and modifications can be made without departing from the spirit and scope of the invention. As will be also be apparent to the skilled practitioner, all combinations of the embodiments and features taught in the foregoing disclosure are possible and can result in preferred executions of the invention. It is therefore intended to cover in the appended claims all such changes and modifications that are within the scope of this invention.

What is claimed is:

1. An absorbent member for use in a disposable absorbent article, said absorbent member comprising:
   a) at least one storage layer having a density of at least about 0.4 g/cm$^3$, which comprises a first absorbent polymer material wherein said first absorbent polymer material has an AAP greater than about 20 g/g; and
   b) an acquisition system comprising an acquisition/storage layer having a density of at least about 0.4 g/cm$^3$, that is substantially free of cellulosic fibers which comprises a second absorbent polymer material, any of said layers comprising said first absorbent polymer material underlying said acquisition/storage layer;
wherein said second absorbent polymer material has a Wet Permeability of at least about 400×10$^{-7}$ (cm$^3$ seconds)/g, a CRC less than about 20 g/g and a ratio of Wet Permeability to SFC of at least about 1.5:1 with respect to said first absorbent polymer material; further wherein said acquisition system provides between about 5% and about 25% of the overall permanent storage capacity of the absorbent member.

2. An absorbent member according to claim 1 wherein said second absorbent polymer also has a free swell rate of at least about 0.1 g/g/sec.

3. An absorbent member according to claim 2 wherein said second absorbent polymer has a free swell rate of at least about 0.2 g/g/sec.

4. An absorbent member according to claim 1 wherein said absorbent member has a caliper less than about 5 mm.

5. An absorbent member according to claim 4 wherein said member has a caliper less than about 4.5 mm.

6. An absorbent member according to claim 4 wherein said absorbent member has a normalized capacity greater than about 0.5 g/cm$^2$.

7. An absorbent member according to claim 6 wherein said absorbent member has a normalized capacity greater than about 1.5 g/cm$^2$.

8. An absorbent member according to claim 4 wherein said absorbent member has an acquisition rate on the fourth gush of less than about 130 seconds.

9. An absorbent member according to claim 1 wherein said absorbent member has an area ratio of less than 1.0.

10. An absorbent core, said absorbent core comprising an absorbent member according to claim 1 and an acquisition layer.

11. An absorbent core according to claim 10 wherein the acquisition layer comprises a material selected from the group consisting of nonwoven materials and curly cellulosic fibers.

12. An absorbent article comprising:
a topsheet having a periphery;
a backsheet joined to said topsheet about at least a portion of said periphery; and
bent member according to claim 1.

13. An absorbent article according to claim 12 wherein said absorbent article has a caliper of less than about 5 mm.

14. An absorbent article according to claim 12 wherein said absorbent article has an acquisition rate on the fourth gush of less than about 130 seconds.

* * * * *